(12) United States Patent
Horton et al.

(10) Patent No.: US 6,454,937 B1
(45) Date of Patent: Sep. 24, 2002

(54) UV LIGHT REACTOR

(75) Inventors: Isaac Horton, Raleigh, NC (US);
Andrew P. Riser, Newbury, OH (US);
Kurt Garrett, Raleigh, NC (US); John F. Forkner, Laguna Beach, CA (US)

(73) Assignee: Remote Source Lighting International, Inc., San Juan Capistrano ( * ) Notice: Subject to any disclaimer, the term of this patent is extended or adjusted under 35 U.S.C. 154(b) by 0 days.

(21) Appl. No.: 09/692,801

(22) Filed: Oct. 20, 2000

Related U.S. Application Data

(63) Continuation of application No. PCT/US99/07874, filed on Sep. 4, 1999.
(60) Provisional application No. 60/081,154, filed on Apr. 9, 1998.

(51) Int. Cl.[7] .................................................. C02F 1/32
(52) U.S. Cl. ........................ 210/192; 250/435; 250/438; 422/186.3
(58) Field of Search ................................. 210/192, 748, 210/764; 422/24, 186.3; 250/435, 437, 438, 434

(56) References Cited

U.S. PATENT DOCUMENTS

| | | | | |
|---|---|---|---|---|
| 1,193,143 A | * | 8/1916 | Henri et al. | |
| 5,006,233 A | * | 4/1991 | Muisener | |
| 5,208,461 A | * | 5/1993 | Tipton | |
| 5,439,595 A | * | 8/1995 | Downey, Jr. | |
| 5,523,001 A | * | 6/1996 | Foeckler, Jr. et al. | |
| 5,661,828 A | * | 8/1997 | Riser et al. | |
| 5,675,153 A | * | 10/1997 | Snowball | |
| 5,682,448 A | * | 10/1997 | Riser et al. | |
| 5,706,376 A | * | 1/1998 | Rykowski et al. | |
| 5,708,737 A | * | 1/1998 | Riser | |
| 5,790,723 A | * | 8/1998 | Riser et al. | |
| 5,790,725 A | * | 8/1998 | Rykowski | |
| 5,839,078 A | * | 11/1998 | Jennings et al. | |
| 5,862,277 A | * | 1/1999 | Riser et al. | |
| 6,090,296 A | | 7/2000 | Oster | |

FOREIGN PATENT DOCUMENTS

DE             4120340 A1  *  12/1992

* cited by examiner

Primary Examiner—Joseph W. Drodge
Assistant Examiner—Terry K. Cecil
(74) Attorney, Agent, or Firm—Stout, Uxa, Buyan & Mullins, LLP; Donald E. Stout

(57) ABSTRACT

A water disinfection system includes a housing having a plurality of risers 207 therein for directing independent columns of water from a manifold at the bottom of the housing. An ultraviolet light source 214 is disposed above the risers to treat the water flowing therein. The UV light source may also be in the form of a fiber optic system (FIG. 4) or a mercury arc lamp including a parabolic reflector 64. Each of the risers can also include notches 304 (FIG. 9) for inducing turbulence to the water flowing thereover in order to ensure that all of the microorganisms receive ultraviolet light. The water flow rate and the light intensity may be adjusted to accommodate different levels of water contamination.

15 Claims, 7 Drawing Sheets

UV LIGHT REACTOR

This application is a continuation under 35 U.S.C. 120 of PCT Application Ser. No. PCT/US99/07874, filed Sep. 4, 1999 the contents of which are expressly incorporated herein by reference, which application in turn claims the benefit under 35 U.S.C. 119(e) of the filing date of U.S. Provisional Patent Application Ser. No. 60/081,154, filed Apr. 9, 1998, the contents of which are herein also expressly incorporated by reference.

BACKGROUND OF THE INVENTION

1. Field of the Invention

This invention relates to water disinfection, and, more particularly, to water disinfection using ultraviolet light.

2. Description of the Related Art

Water is an important resource that is used in many commercial purposes, such as agriculture and aquaculture, as well as for household use. Furthermore, clean water that is free from unhealthy chemicals and microorganisms is becoming a more precious resource as populations increase.

Water is often treated prior to it being used for commercial purposes or household use. Disinfection of the water to remove microorganisms is a common treatment. The use of ultraviolet ("UV") light as a disinfecting agent is not a new idea. Downs and Blunt discovered that sunlight destroyed some bacteria in 1878. Since their discovery, scientists have performed experiments to determine the conditions when UV radiation can be used as a disinfecting agent, and have determined the doses required to kill many microorganisms. Disinfection is generally accomplished using heat, chemicals, or UV light. UV light is particularly desirable since it leaves no toxic residue in the water.

The prior art has many applications of treating water with UV light to kill microorganisms. These applications involve flowing water going past a UV light source. In some applications, water flows past a bank of light sources. This application is problematic as the light sources may be extremely heavy, making them difficult to replace. In another application, a UV light source is suspending axially in a pipe and water flows past it. The maintenance of this type of light source may also be difficult. Some problems are common to both applications. The light sources become fouled with use from being in continual contact with the water flow, thereby reducing the efficiency of the light sources. Further, the UV light is often not efficiently absorbed by the water. Instead, the UV light is absorbed by the walls of the vessels in which the UV lights are disposed Therefore, a water disinfection system using UV light that does not incur fouling of the light source and has efficient absorption of the UV light by water is needed. It is further needed a system that permits quick and simple maintenance of the UV light source.

SUMMARY OF THE INVENTION

In an aspect of the invention, a water disinfection system comprises a vertical water column directing channel and an ultraviolet light beam generator system. The vertical water column directing channel has an open top end and a channel interior space extending from the open top end. The ultraviolet light beam generator system has an ultraviolet light beam exit. The ultraviolet light beam generator system is arranged such that an ultraviolet light beam generated therein exits through the ultraviolet light beam exit, passes through the channel top open end, and enters the channel interior space.

In a further aspect of the invention, the channel open top end comprises a top end interior cross-section. Additionally, the ultraviolet light beam produced by the ultraviolet light beam generator system has a light beam cross section that is the substantially the same as the top end interior cross-section or eclipses the top end interior cross-section.

In a further aspect of the invention, the ultraviolet light beam produced by the ultraviolet light beam generator system comprises ultraviolet light in a spectral band of approximately 242 nm to 270 nm.

In a further aspect of the invention, the vertical water column directing channel comprises a riser having a length from the open top end to a bottom end and a substantially constant interior cross-section through the riser length. The top end interior cross-section is generally equal to the riser interior cross-section. In a still further aspect of the invention, the riser is generally cylindrical in shape.

In a further aspect of the invention, a water column turbulating feature located at the channel top open end. In a still further aspect of the invention, the water column turbulating feature is one or more notches in the vertical water column directing channel at the open top end.

In a further aspect of the invention, the vertical water column directing channel comprises an untreated water entrance into the channel's interior space. The channel's interior space also comprises a channel interior space portion being defined by the top open end and the untreated water entrance. The channel interior space portion has a continuous volume therein with a constant latitudinal cross-section and an axial length extending from the open top end and through the channel interior space portion. Further, the ultraviolet light beam generator system is arranged such that the ultraviolet light beam is directed through the open top end along the channel interior space portion continuous volume.

In a still further aspect of the invention, the ultraviolet light beam has a water absorption distance that is less than the continuous volume axial length. As a result, the ultraviolet light beam is substantially absorbed by water flowing through the vertical water column directing channel and not by the vertical water column directing channel.

In a further embodiment of the invention, the ultraviolet light beam generator system comprises a lamp and a reflector. The lamp produces dispersed light to be used to form the ultraviolet light beam. The reflector may be parabolic or elliptical and positioned to direct the dispersed light from the lamp. In a still further aspect of the invention, the lamp is a medium pressure mercury arc lamp. In an aspect of the invention, the ultraviolet light beam generator system comprises a fiber optic system.

In a further aspect of the invention, there may be a plurality of vertical water column directing channels. The ultraviolet light beam generator system comprises a plurality of ultraviolet light beam exits. The ultraviolet light beam generator system is arranged such that ultraviolet light beams generated therein exit through the ultraviolet light beam exits, pass through the channels top open ends and enter the channels interior spaces. A lamp in ultraviolet light beam generator system may generate the ultraviolet light beams for more than one exit and/or riser.

In a further aspect of the invention, an uninterrupted air space is disposed between the channel open top end and the ultraviolet light beam exit of the ultraviolet light beam generator system. In this case, the water has limited, if substantially non-existent, opportunities to contact the surface of the exit and start fouling it.

In an aspect of the invention, a process of disinfecting water comprises the steps of forming a vertically oriented column of flowing water to be disinfected and directing an ultraviolet beam into the column. The flowing water moves from a bottom of the column to a top of the column, at which point the flowing water flows in a general radial direction away from the column top. The ultraviolet light beam is directed through an uninterrupted air space, the flowing water column top and into the column of water. The ultraviolet light beam disinfects the flowing water prior to the flowing water flowing away from the flowing water column top In a further aspect of the invention, the column of flowing water is formed by directing the flowing water through a vertically oriented channel. In a still further aspect of the invention, the vertically oriented channel is a cylindrical riser.

In a further embodiment of the invention, the light beam is collimated and has a latitudinal cross-section generally the same as, or bigger than, a latitudinal cross-section of the flowing water column top. Further, the collimated ultraviolet light beam is aligned with the column of flowing water such that the collimated ultraviolet light beam is generally coincident with the column of flowing water after the collimated ultraviolet light beam passes through the flowing water column top.

In a further aspect of the invention, the light beam. is substantially absorbed by the column of flowing water.

In a further aspect of the invention, a volumetric flow rate of the column of flowing water and an intensity of the ultraviolet light beam is chosen to achieve a predetermined microorganism survival rate. In a still further aspect of the invention, the using a microorganism survival equation, the microorganism survival equation is:

$$N_1/N_0 = e^{-k(It)}$$

where $N_1$=Final number of living organisms $N_0$=Initial number of living organisms −k=rate constant I=Intensity of the ultraviolet light beam (mW/cm$^2$)

t=time required to achieve the desired kill percentage and the volumetric flow rate of the column of flowing water is a light absorbance volume divided by t, wherein the light absorbance volume is a volume of the column of flowing water in which substantially all of the ultraviolet light beam is absorbed.

DESCRIPTION OF THE PREFERRED EMBODIMENTS

Figure 1:
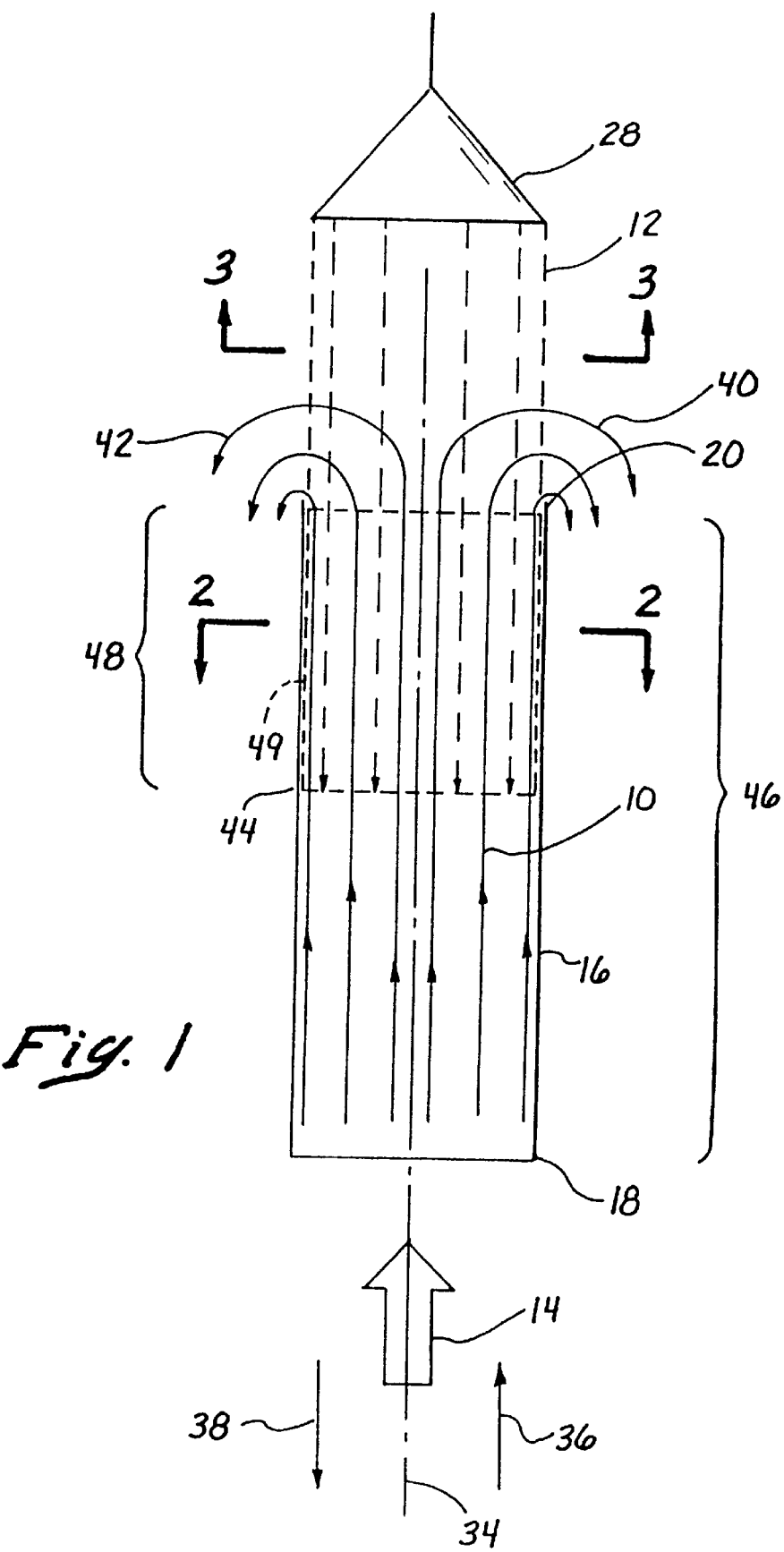
FIG. 1 shows an axial cross-section of a vertical riser with a water column moving upwardly therethrough and a UV light beam directed downwardly through the water column.
Figure 3:
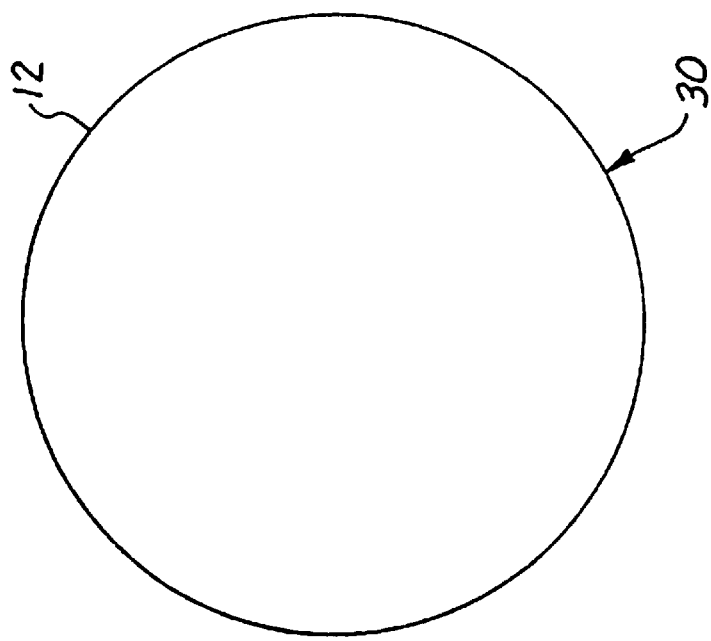
FIG. 3 show the cross-section 3—3 of FIG. 1, which is an upward view of the UV light beam.
Figure 2:
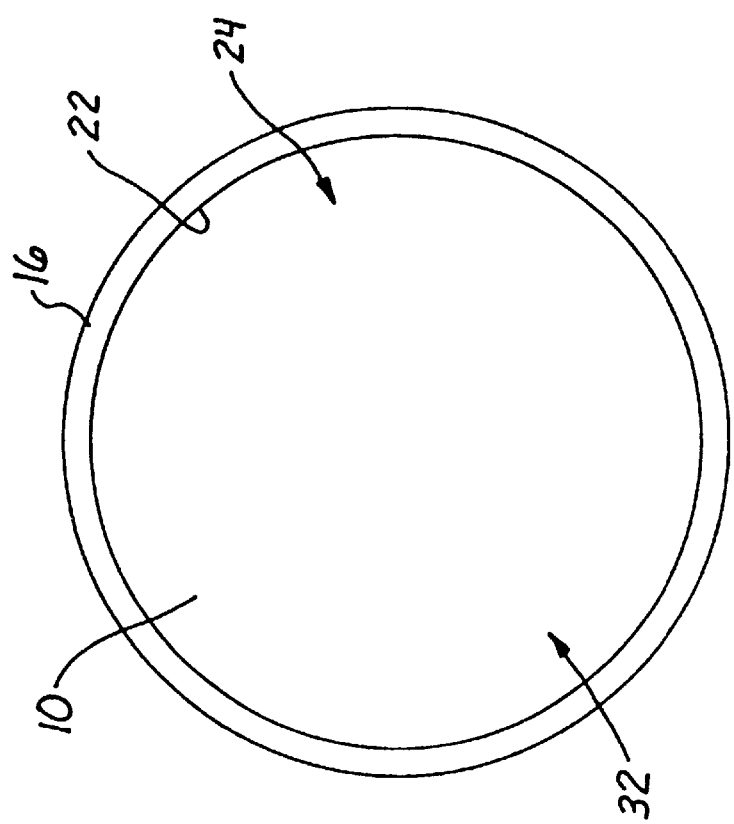
FIG. 2 shows the cross-section 2—2 of FIG. 1, which is a downward view of the vertical riser.

Now referring to the figures, wherein like reference numbers refer to like elements throughout the figures, and specifically to FIGS. 1, 2, and 3, a water column 10 is shown being disinfected by an UV light beam 12. The water column 10 originates from a stream of water 14 that enters a vertical riser 16 at a riser entrance 18. The riser 16 extends vertically from the riser entrance 18 and terminates at a riser end 20. The riser also has an axis 34 that defines an upwards axial direction 36 and a downwards axial direction 38. In a preferred embodiment of the invention, the riser 10 has a circular riser inner perimeter 22 which defines a riser circular internal cross-section 24 that is substantially constant throughout the riser 10 as the riser is cylindrical in shape. Other embodiments of the invention may have risers of other cross-sections, varying cross-sections, or have other vertical water column directing channels.

The water column 10 flows through the riser 16 in the upwards vertical direction 36. Since the riser 16 forms the water column 10, the column has a column circular cross-section 32 that is equivalent to the riser internal cross-section 24. Other embodiments of the invention may have differently shaped cross-sections and perimeters. The water column 10 terminates at the water column end 40 that is shown to be substantially co-existent with the riser end 20. Other embodiments of the invention may have the water column end 40 located above the riser end 20. At the water column end 40, the disinfected water 42 is shown flowing in a general radial direction away from the column top and down a riser exterior surface 44 in the downward axially direction 38. Other embodiments of the invention may have the disinfected water 42 flow in other directions.

The UV light beam 12 is generated by a light source 28 and directed in the downwards axial direction 38 through the water column end 40 and into the water column 10. The light source 28 is not in direct contact with the water column end 40, resulting in reducing, if not eliminating, inefficiencies due to fouling of the light source. Embodiments of the invention comprises an uninterrupted air space adjacent to the water column 10 that the light beam 12 passes through prior to entering the water column.

The UV light beam 12 has a circular cross-section 30. In the preferred embodiment of the invention, the UV beam cross-section 30 is substantially the same as the riser cross-section 24. By being substantially the same, all of the UV light beam 12 enters the water column 10 and efficiently functions as a disinfecting agent. Other embodiments of the invention may have a UV light beam that substantially eclipses the riser cross-section 24 or have a UV light beam of other cross-sections.

In a preferred embodiment of the invention, the UV light beam 12 is substantially absorbed by the water column 10 within a water absorption distance 48 of the riser end 20. The beam 12 is substantially absorbed because the water absorption distance 48 is shorter than a riser length 46, which is the distance between the riser entrance 18 and the riser end 20. By having the riser length 46 longer than the water absorption distance 48, the UV light beam 12 is absorbed by the water column 10, and not by a wall, plate, or some other structure (not shown) at the riser entrance 18.

The portion of the water column 10 in which the UV light beam 12 is substantially absorbed into is a light absorbance volume 49. The light absorbance volume 49 in the shown embodiment of the invention is the water absorption distance 48 times the riser cross-section 24. In an embodiment of the invention, the ultraviolet light beam 12 is collimated and aligned with the riser 16 such that the collimated ultraviolet light beam is generally coincident with the column of flowing water in the riser. In other embodiments of the invention have the UV light beam 12 may have the light absorbance volume be only a portion of the channel through which the water flows. The channel portion is of a continuous volume with a constant latitudinal cross-section such that the light beam 12 is absorbed by the water in the channel portion and not by the channel itself.

The intensity of the UV light beam 12 and the residence time of the vertical riser are predetermined based on the type and concentration of the micro-organisms in the stream of water 14. Different exposures to UV light is required to kill different micro-organisms. For a 90% kill, with the UV light moving through air, the exposures are:

| Organism | Exposure ($\mu$Ws/cm$^2$) |
|---|---|
| Bacteria | 1,500–20,000 |
| Virus | |
| E. Coli (dry) | ~250 |
| E. Coli (wet) | ~5,000 |
| Yeast | 3,000–6,000 |
| Mold Spores | 15,000–45,000 |

Although some disagreement of opinion exists, it is thought that the disinfection of water requires exposure of five to fifty times greater that in air. Other factors affect the amount of exposure, such as water turbidity, water depth, and water clarity.

Different water streams requires different exposure to be treated based on the above listed factors, and others, each stream of water need to be tested to determine required exposure to UV light. The microorganism survival equation is:

$$N_1/N_0 = e^{-k(It)}$$

where $N_1$=Final number of living organisms $N_0$=Initial number of living organisms −k=rate constant I=Intensity of the UV light (mW/cm$^2$)

t=time required to achieve the desired kill percentage

Upon determining I and t, the volumetric flow rate of the column of water is the light absorbance volume 49 divided by t for any I. Embodiments of the invention may have means for adjusting the residence time and/or the light intensity based on input concerning changes in the characteristics of the water being treated. Further discussions concerning treating water with ultraviolet light are disclosed in U.S. Pat. Nos. 5,208,461 and 5,675,153, which are incorporated by reference herein in their entireties.

Different embodiments of the invention may have different light sources for generating the UV beam of light. In general, a lamp, or light pump, generates dispersed light comprising UV spectrum light and non-UV spectrum light. A UV light beam forming means for filtering a substantial amount of the non-UV spectrum light from the dispersed light, and for focusing the remaining light into the UV light beam 12 is used to provide the UV light beam 12.

Figure 4:
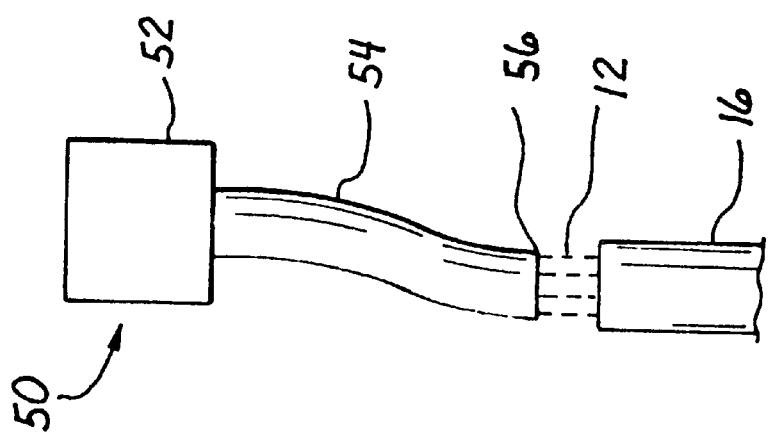
FIG. 4 shows a schematic view of an optical fiber system for providing UV light to disinfect water.

Referring to FIG. 4, one embodiment of the invention uses a light source 50 comprised of a light pump 52 with an optical fiber 54 connected thereto to provide the UV light beam 12. The optical fiber 54 has an end 56 through which the UV light beam 12 emerges. Light sources 50 that produce an UV light beam are known in the art.

Figure 5:
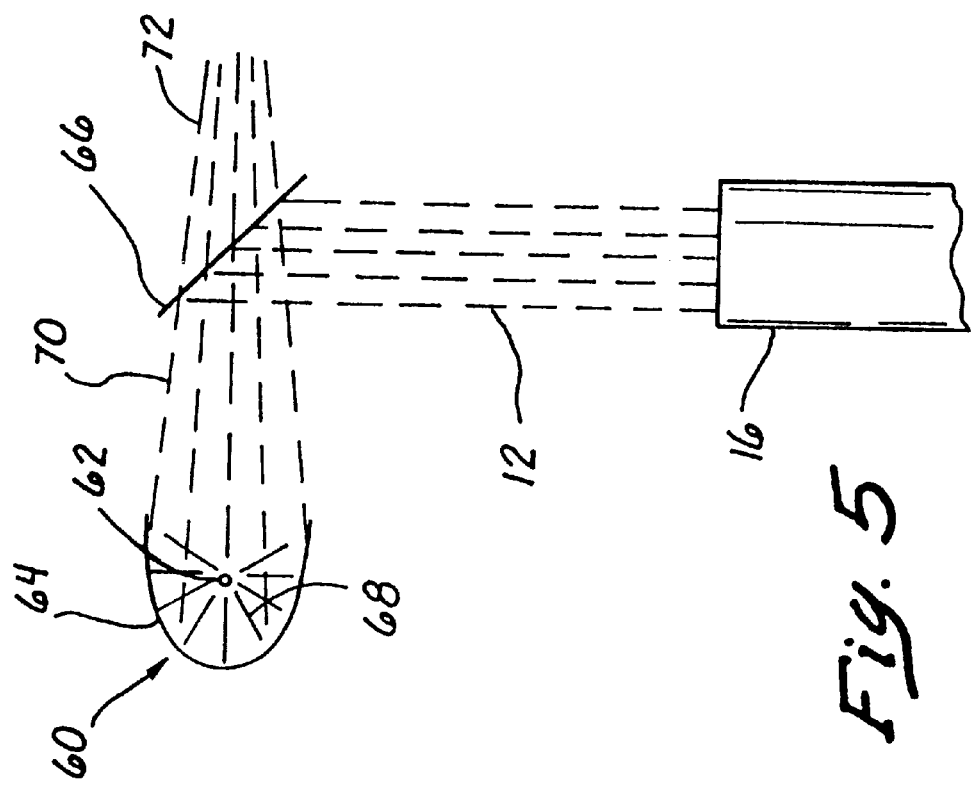
FIG. 5 shows a schematic view of a parabolic reflector system for providing UV light to disinfect water.

Referring now to FIG. 5, one embodiment of the invention uses a light source 60 comprised of a mercury lamp 62, a parabolic reflector 64, and a cold mirror 66. In an embodiment of the invention, the mercury lamp 62 may be a low pressure mercury lamp. A low pressure mercury lamp is of relatively low cost and 95% of the light it emits is in a narrow band centered on approximately 254 nm −260 nm, making it very effective. In another embodiment of the invention, the mercury lamp 62 may be a medium pressure lamp. Other embodiments of the invention may use other lamps.

During operation, the mercury lamp 62 emits a dispersed light 68 which is reflected and directed by the parabolic reflector 64 as a prefiltered beam 70 to the cold mirror 66. In one embodiment of the invention, the cold mirror 66 filters out the non-UV spectrum in the prefiltered beam 70 by reflecting only UV spectrum light to form the UV light beam 12. In other embodiments of the invention, the UV light beam 12 has an UV spectrum of substantially approximately 242 to 270 nm or approximately 240 to 320 nm. Other embodiments of the invention may use other filtering means which will result in other UV spectrum ranges for the UV light beam 12. The non-UV spectrum light passes through the cold mirror 66 and forms a non-UV spectrum light beam 72. Additionally, by filtering out the non-UV spectrum light, the "hotter" non-UV light does not enter the water column 12, thereby heating it up and promoting algae growth.

Other embodiments of the invention may use other types of UV light generation systems, such as those disclosed in U.S. Pat. Nos. 5,661,828; 5,682,448; 5,706,376; 5,708,737; 5,790,723; 5,790,725; 5,862,277; and 5,892,867, the contents of which are expressly incorporated herein by reference.

Figure 6:
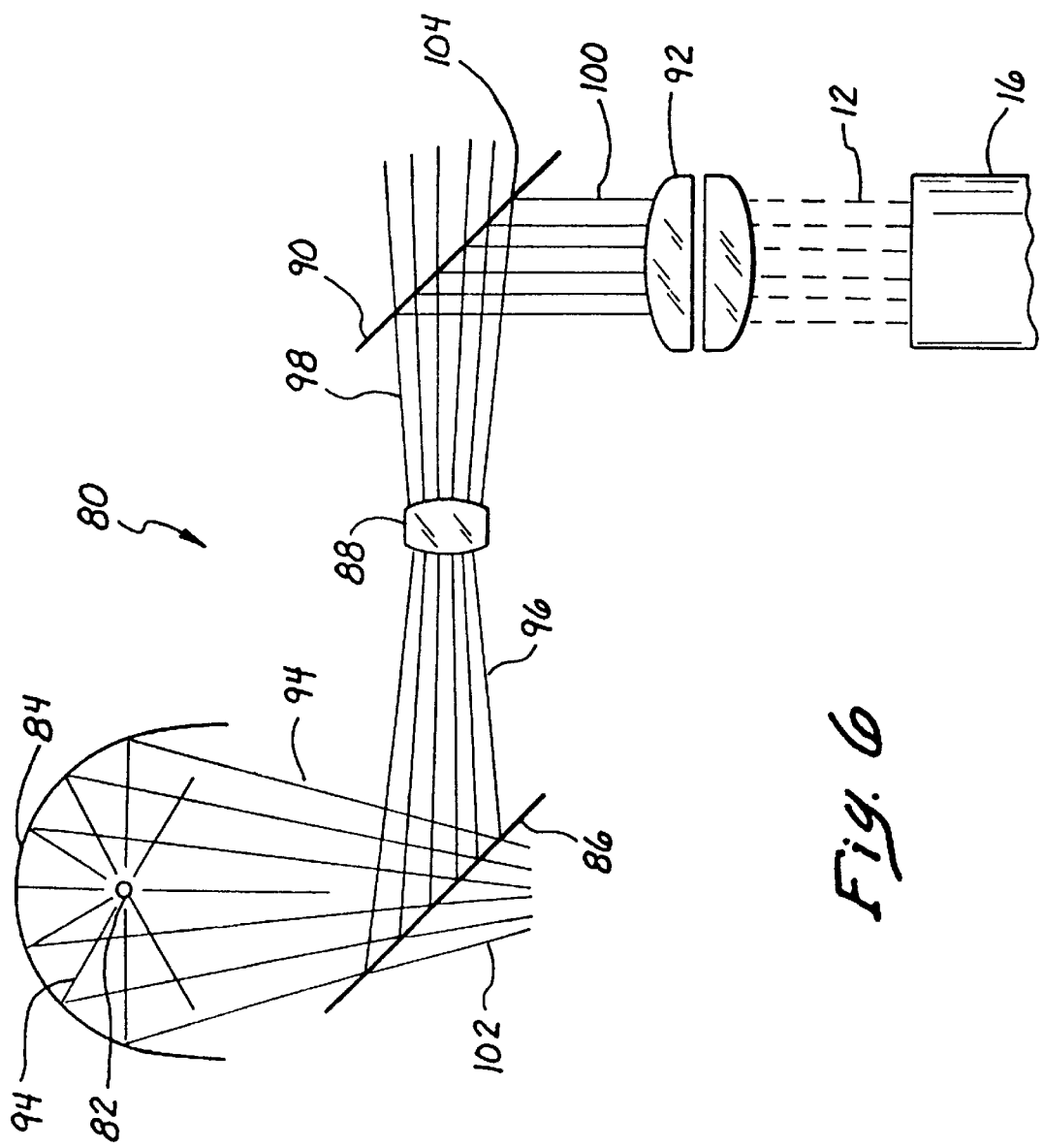
FIG. 6 shows a schematic view of an elliptical reflector system for providing UV light to disinfect water.

Now referring to FIG. 6, one embodiment of the invention uses a light source 80 comprised of a mercury lamp 82, an elliptical reflector 84, a first cold mirror 86, a lens array 88, a second cold mirror 90 and a collimating lens 92 to produce the UV light beam 12. The mercury lamp 82 has similar characteristics as the previously described mercury lamp 62 and produces a dispersed light 94. The elliptical reflector 84 focusses and directs the dispersed light 94 as a first prefiltered light beam 94 to the first cold mirror 86. The first cold mirror 86 operates in a similar fashion as the cold mirror 66 previously described, with a first non-UV spectrum light beam 102 extending from the mirror, and a second prefiltered light beam 96 reflecting off of the mirror. The second prefiltered light beam 96 is directed through the lens array 88 to form a third prefiltered beam 98. The third prefiltered beam 98 is directed to the second cold mirror 90, with a precollimated UV light beam 100 reflecting off of the mirror, and a second non-UV spectrum light 104 extending from the mirror. The first and second cold mirrors 86 and 90 may be the same, or have different filtering characteristics. The precollimated UV light beam 100 is directed through collimating lenses 92 to produce the UV light beam 12. Other embodiments of the invention may not provide a collimated UV light beam 12 and, therefore, not have the collimating lenses 92.

Other embodiments of the invention may use other lamps, reflectors, spectrum filters, lenses, and arrangements thereof to produce the UV light beam 12.

Figure 7:
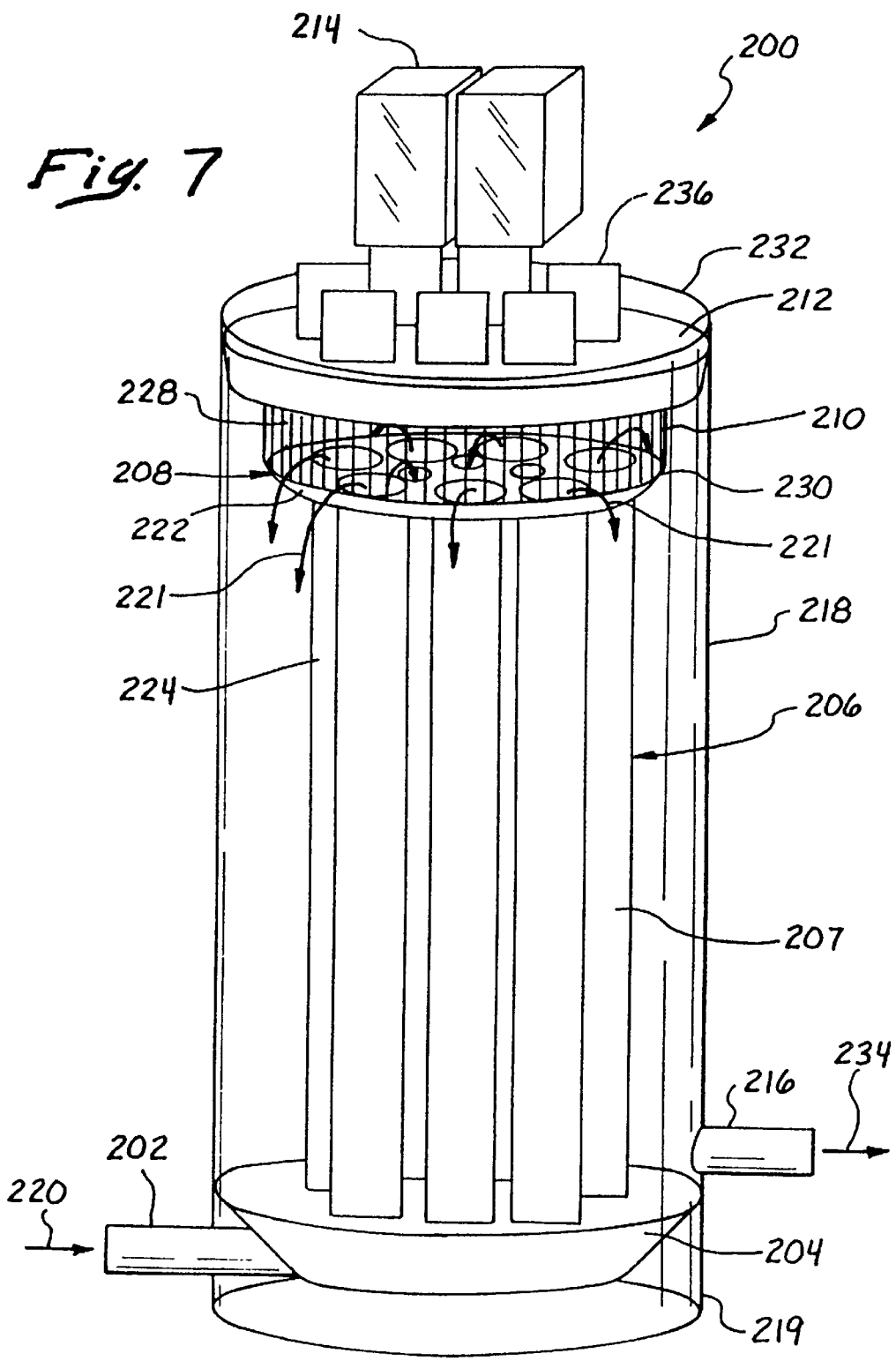
FIG. 7 shows a UV light reactor.

Referring now to FIG. 7, a UV light reactor 200 for disinfecting an influent stream 220 is comprised of an inlet 202, a manifold 204, an array of risers 206, a reactor interface plate 208, an air spacer 210, a holding plate 212, UV light pumps 214, and an outlet 216. The manifold 204, array of risers 206, the reactor interface plate 208, the air spacer 210, and the holding plate 212 are contained in a reactor wall 218 which is shown in ghost lines. The reactor wall 218 is shown to be cylindrical and vertical. Other embodiments of the invention may have reactor walls of other shapes.

The influent stream 220 flows into the reactor 200, where it is treated with the UV light pumps 214, and flows out of the reactor 200 as an effluent stream 234. The influent stream 220 flows through the inlet 202, past the reactor wall 218 and into the manifold 204. The manifold is round and fits against the interior of the reactor wall 218 at the reactor bottom 219. The manifold 204 distributes the influent stream 220 to the array of risers 206, where a column of vertically moving water is created in each riser (not shown). The array of risers 206 comprises seven risers 207 arranged in a circular formation. Other embodiments of the invention may have more or less risers, and the risers may be arranged in other suitable formations. The array of risers 206 extends vertically from the manifold 204 to the reactor interface plate 208. The reactor interface plate 208 is round and has a diameter less than the inner diameter of the reactor wall 218. The now disinfected water 221 emerges from the array of risers 206 through the plate 208, flows over the plate, and descends downwardly either by flowing over an outside edge 222 of the plate or by flowing through internal holes 224 in the plate. The disinfected water 221 descends to the bottom of the reactor 200 and exits through the outlet 216 as the effluent stream 234.

The UV light pumps 214, which disinfect the influent stream 220, are located at the top 232 of the reactor 200. The reactor 200 has seven UV light pumps 214 (two shown) mounted on light pump supports 236. The light pump supports 236 are cylindrical in shape and are disposed on the holding plate 212 over holes (not shown). The holding plate 212 is round and fits against the top 232 of the reactor wall 218. The supports 236 are aligned with the risers 207 such that each riser has a light pump 214. The holes enable an UV light beam (not shown) to travel from the light pumps 214 to its respective riser 207 to disinfect the column of water therein. With one light pump 214 per riser 206, the light pump is relatively light, compact, and readily replaceable if needed. Other embodiments of the invention may have one light pump providing UV light to more than one riser.

To inhibit fouling of the light pumps 214, an air space 228 separates the flow of water through the reactor 200 from the UV light pumps 214. The air space 228 is formed by air spacers 210 vertically separating the reactor interface plate 208 and the holding plate 212. The air spacer 210 is a stainless steel cylinder that is slotted to permit the disinfected water to flow therethrough. A bottom end 230 of the air spacer 210 rests at the edge 222 of the interface plate 208. The holding plate 212 is disposed on top of the air spacer 210. Other embodiments of the invention may use other means to inhibit or prevent water from fouling the light sources. Other embodiments may omit the air spacer and use other suitable means for creating the air space 228.

Figure 8:
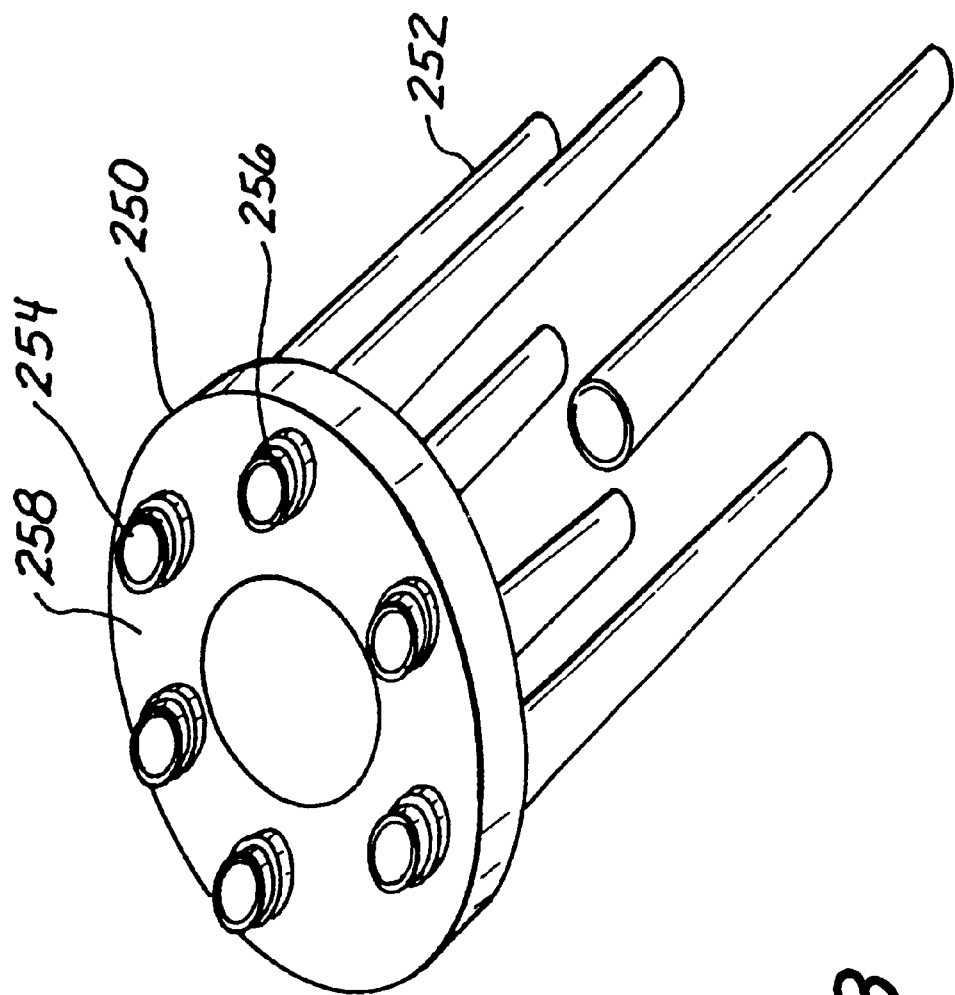
FIG. 8 shows an isometric view of a reactor interface with nipples from a UV light reactor.

Now referring to FIG. 8, in one embodiment of the invention, a reactor interface plate 250 is annularly shaped and has six risers 252 connected to it. The risers 252 enter the underside of the plate 250 at holes 254. On the top surface 258 of the plate 250, nipples 256 extend from the holes 254. The nipples 256 encourage turbulence at the top of the column of water (not shown) in the risers 252. By having turbulence at the top of the column, the microorganisms are more effectively radiated by the UV light beam (not shown). Without the turbulence, some microorganisms in the water may be shielded from the UV light by other microorganisms or debris in the water and not killed. Other embodiments of the invention may have other means of creating turbulence at the top of the column of water.

Figure 9:
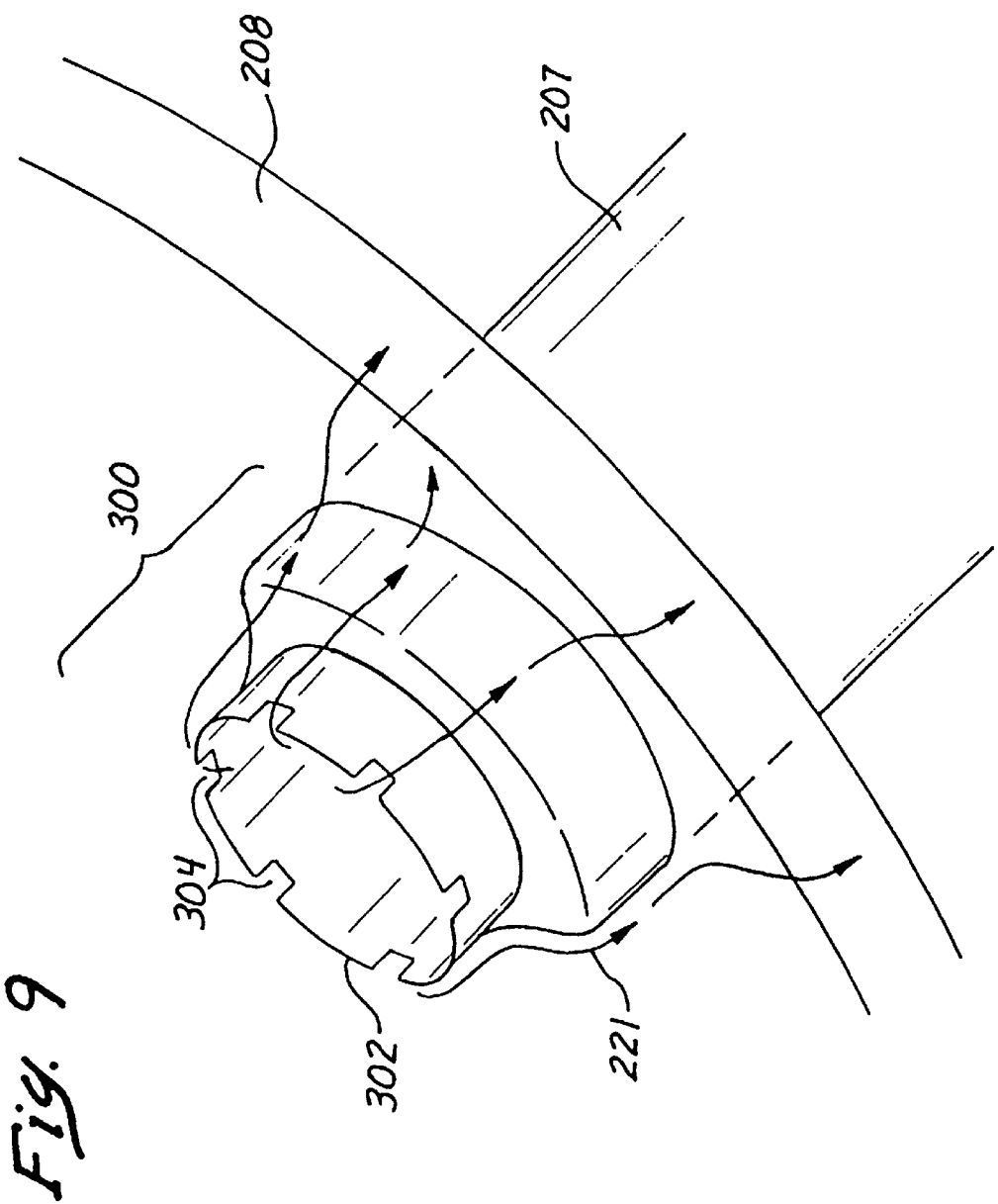
FIG. 9 shows a detailed view of a nipple having a notched rim.

Now referring to FIG. 9, an embodiment of the invention is shown with a riser 207 terminating at a nipple 300 having a notched rim 302. The notched rim 302 has a plurality of notches 304 around its circumference. The column of vertically moving water (not shown) exits the riser at the nipple 300 as disinfected water 221. The volumeric flow rate of the column of vertically moving water is such that a majority, if not substantially all, of the water flows out of the riser through the notches 304 in the rim 302. By having the disinfected water 221 flowing through the notches 304, the top of the water column has turbulent flow. Embodiments of the invention may have the nipple 300 mounted to the plate 208, mounted to the terminating end of the riser, removable mounted to either one, or mounted in some other suitable fashion. Other embodiments of the invention may have other turbulating features to create turbulence flow at the top of the water column.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A water disinfection system, comprising:
   a housing having a vertically-oriented axis;
   a water inlet disposed on a lower end of said housing;
   a water outlet disposed on said lower housing end;
   a plurality of vertically oriented channels within said housing, each accommodating an independent flowing water column therein, each of said plurality of channels having an open top end and a channel interior space extending downwardly from said top end to a bottom end, each said bottom end spaced from a bottom of said housing to form a common manifold in communication with the inlet for inputting water into said channels; and
   an ultraviolet (UV) light source disposed above said plurality of vertically oriented channels for directing UV light downwardly through the open top end of each of said channels.

2. The water disinfection system as recited in claim 1, wherein said housing comprises a sidewall, and said water inlet is disposed in said sidewall.

3. The water disinfection system as recited in claim 2, wherein water flowing into said housing through said water inlet enters said housing in a direction transverse to said housing axis.

4. The water disinfection system as recited in claim 1, wherein the UV light has a wavelength within a spectral band of approximately 242 nm to 270 nm.

5. The water disinfection system as recited in claim 1, wherein each of the plurality of channels comprises a riser having a length from the open top end thereof to a bottom end thereof, and has a substantially constant interior cross-section throughout the riser length.

6. The water disinfection system as recited in claim 5, wherein each of said risers is generally cylindrical in shape.

7. The water disinfection system as recited in claim 1, and farther comprising a water column turbulating feature disposed at the top end of each of said channels.

8. The water disinfection system as recited in claim 7, wherein said water turbulating feature comprises at least one notch in the channel top end.

9. The water disinfection system as recited in claim 1, wherein the UV light source comprises a lamp that produces dispersed light to be used to form a UV light beam and a parabolic or elliptical reflector positioned to direct the dispersed light from said lamp.

10. The water disinfection system as recited in claim 9, wherein the lamp is a medium pressure mercury arc lamp.

11. The water disinfection system as recited in claim 1, wherein the UV light source comprises a fiber optic system.

12. The water disinfection system as recited in claim 1, wherein the UV light source comprises a plurality of UV light exits, the UV light source being arranged so that a UV light bean generated by said UV light source exits through each of said UV light exits, passes through a corresponding channel top end, and enters The interior space of said corresponding channel.

13. The water disinfection system as recited in claim 1, and further comprising an uninterrupted air space disposed between the open top ends of each of said plurality of channels and said UV light source.

14. A liquid disinfection system, comprising:

a housing having a vertically-oriented axis;

a liquid inlet disposed on said housing;

a liquid outlet disposed on said housing;

a plurality of vertically oriented channels, each accommodating an independent flowing liquid column therein, each of said plurality of channels having an open top end and a channel interior space extending downwardly from said top end; and an ultraviolet (UV) light source disposed above said vertically oriented channels for directing UV light downwardly through the open top end of each said channel, said UV light source comprising an illumination source, and a plurality of optical components for directing illumination from said illumination source in a desired direction, said optical components including fiber optic lines for transmitting said illumination, wherein none of said optical components are submersed in liquid treated by said system.

15. A liquid disinfection system, comprising:

a housing having a vertically-oriented axis;

a liquid inlet disposed on said housing;

a liquid outlet disposed on said housing;

a plurality of vertically oriented channels each accommodating an independent flowing fluid column therein, each of said plurality of channels having an open top end and a channel interior space extending downwardly from said top end; and a single ultraviolet (UV) light source disposed above said plurality of vertically oriented channels for directing UV light downwardly through the open top end of each of said channels, wherein said single UV light source comprises a plurality of light exits corresponding in number to said plurality of channels such that light from each of said light exits is directed to the open top end of a corresponding one of said plurality of channels.

* * * * *